(12) United States Patent
Liu

(10) Patent No.: US 11,326,940 B2
(45) Date of Patent: May 10, 2022

(54) AMBIENT LIGHT SIGNAL ADJUSTMENT METHOD, CHIP AND ELECTRONIC EQUIPMENT

(71) Applicant: Shenzhen Goodix Technology Co., Ltd., Shenzhen (CN)

(72) Inventor: Chang Liu, Shenzhen (CN)

(73) Assignee: Shenzhen Goodix Technology Co., Ltd., Shenzhen (CN)

( * ) Notice: Subject to any disclaimer, the term of this patent is extended or adjusted under 35 U.S.C. 154(b) by 127 days.

(21) Appl. No.: 17/032,441

(22) Filed: Sep. 25, 2020

(65) Prior Publication Data

US 2021/0123801 A1 Apr. 29, 2021

(30) Foreign Application Priority Data

Oct. 25, 2019 (CN) .......................... 201911021430.0

(51) Int. Cl.
*G01J 1/42* (2006.01)
*G01J 1/44* (2006.01)

(52) U.S. Cl.
CPC ............... *G01J 1/4204* (2013.01); *G01J 1/44* (2013.01)

(58) Field of Classification Search
CPC .................................. G01J 1/4204; G01J 1/44
See application file for complete search history.

(56) References Cited

U.S. PATENT DOCUMENTS

| 5,644,385 A | 7/1997 | Mizuno |
| 9,615,427 B1 | 4/2017 | Narayanan et al. |
| 9,662,053 B2 | 5/2017 | Richards et al. |
| 2005/0187448 A1 | 8/2005 | Petersen et al. |

(Continued)

FOREIGN PATENT DOCUMENTS

| CN | 101944897 A | 1/2011 |
| CN | 105491943 A | 4/2016 |

(Continued)

OTHER PUBLICATIONS

Chinese Office Action dated Aug. 13, 2020 in corresponding Chinese Application No. 201911021430.0; 20 pages.

(Continued)

*Primary Examiner* — Que Tan Le
*Assistant Examiner* — Don J Williams
(74) *Attorney, Agent, or Firm* — Maier & Maier, PLLC

(57) ABSTRACT

An ambient light signal adjustment method, a chip and electronic equipment. The method includes: receiving a first ambient light signal which is an ambient light signal acquired by a photo plethysmor graph (PPG) sensor; then determining, according to an intensity of the first ambient light signal automatically, whether to turn on an ambient light cancellation circuit which is configured to adjust the first ambient light signal according to the intensity of the first ambient light signal; and if it is determined to turn on the ambient light cancellation circuit, then adjusting a cancellation signal intensity of the ambient light cancellation circuit automatically to enable an intensity of the adjusted first ambient light signal to be within a preset range. Adjustment of the ambient light signal acquired by the PPG sensor is realized, thereby ensuring accuracy of a wearable device to detect a physiological characteristic of a user.

20 Claims, 5 Drawing Sheets

(56) References Cited

U.S. PATENT DOCUMENTS

| | | | |
|---|---|---|---|
| 2014/0275852 A1* | 9/2014 | Hong | A61B 5/0002 600/479 |
| 2014/0288435 A1 | 9/2014 | Richards et al. | |
| 2019/0175037 A1 | 6/2019 | Gunturi et al. | |
| 2019/0298237 A1 | 10/2019 | Isaacson et al. | |

FOREIGN PATENT DOCUMENTS

| | | | |
|---|---|---|---|
| CN | 105852841 A | 8/2016 |
| CN | 106559095 A | 4/2017 |
| CN | 109863703 A | 6/2019 |
| CN | 109923785 A | 6/2019 |
| CN | 110604559 A | 12/2019 |
| JP | 2019134089 A | 8/2019 |
| WO | 2016/011173 A1 | 1/2016 |

OTHER PUBLICATIONS

Jongpal Kim, et al. "Ambient Light Cancellation in Photoplethysmogram Application Using Alternating Sampling and Charge Redistribution Technique." 2015 37th Annual International Conference of the IEEE Engineering in Medicine and Biology Society (EMBC). IEEE. Milan, Italy. Aug. 25, 2015. pp. 6441-6444. XP032811627.
Extended European Search Report dated Feb. 11, 2021, in connection with corresponding EP Application No. 20199848.1; 32 pages.
Office Action dated Nov. 29, 2021 in Korea Patent Application No. 10-2020-0126578; with English translation 11 pgs.
International Search Report dated Oct. 13, 2020, in connection with corresponding International Application No. PCT/CN2020/100991; 5 pages.

* cited by examiner

AMBIENT LIGHT SIGNAL ADJUSTMENT METHOD, CHIP AND ELECTRONIC EQUIPMENT

CROSS-REFERENCE TO RELATED APPLICATIONS

This application claims priority to Chinese Patent Application No. 201911021430.0, filed on Oct. 25, 2019, which is hereby incorporated by reference in its entirety.

TECHNICAL FIELD

The present disclosure relates to the technical field of wearable devices and, in particular, to an ambient light signal adjustment method, a chip and electronic equipment.

BACKGROUND

With development of a smart device, the smart device has more and more functions. In order to detect health status of a human body, a sensor (e.g., a sensor disposed in proximity to the human body, above the human body, or close to an external body surface of the human body in other ways) in the smart device (e.g., a wearable device) can be used for detection. The wearable device can not only monitor health status of a wearer's body for a long term, but also allow the wearer to perform normal daily activities, travelling and commuting, or participate in other activities. The health status of the human body monitored by such wearable device may include a heart rate, a blood oxygenation, an activity level, a blood pressure, a galvanic skin response, or other information about the wearer's body.

In the prior art, detection on status of a wearer's human body using the wearable device is usually realized by photoelectric detection. Using detection of a heart rate of a human body as an example, light of a certain wavelength is transmitted by a light transmitter in the wearable device and is incident into a skin tissue. Upon reflection, scattering and absorption from the skin tissue, a part of the light can be emitted from the skin surface and received by a light receiver in the wearable device. During this process, since a blood volume of a subcutaneous tissue presents a pulsatile change responsive to a heart rhythm, a light intensity signal received by the light receiver also presents a pulsatile change accordingly. A photo plethysmor graph (PPG) indicating the blood volume of the subcutaneous tissue changing with a pulse can be obtained by means of converting the light intensity signal received by the light receiver into an electrical signal, and a heart rate value can be calculated from this.

However, in the prior art, during detection on the health status of the human body by the wearable device, if ambient light is too intense, a received light signal will exceed a tolerance range of a back-end circuit, thereby affecting accuracy of a detection result of the wearable device.

SUMMARY

The present disclosure provides an ambient light signal adjustment method, a chip, and electronic equipment, which realize adjustment of an ambient light signal acquired by a PPG sensor, thereby ensuring accuracy of a wearable device to detect a physiological characteristic of a user.

In a first aspect, an embodiment of the present disclosure provides an ambient light signal adjustment method, including:

receiving a first ambient light signal, where the first ambient light signal is an ambient light signal acquired and output by a PPG sensor;

determining, according to an intensity of the first ambient light signal automatically, whether to turn on an ambient light cancellation circuit, where the ambient light cancellation circuit is configured to adjust the first ambient light signal according to the intensity of the first ambient light signal; and if it is determined to turn on the ambient light cancellation circuit, adjusting a cancellation signal intensity of the ambient light cancellation circuit automatically according to the intensity of the first ambient light signal to enable an intensity of the adjusted first light signal to be within a preset range.

In the embodiment of the present disclosure, by means of determining, according to the intensity of the ambient light signal, whether to turn on the ambient light cancellation circuit, and adjusting, after the ambient light cancellation circuit is turned on, the cancellation signal intensity of the ambient light cancellation circuit automatically to enable the intensity of the adjusted first ambient light signal to be within the preset range all the time, adjustment of the ambient light signal acquired by the PPG sensor is realized, thereby ensuring accuracy of a wearable device to detect a physiological characteristic of a user.

In a possible implementation, the determining, according to an intensity of the first ambient light signal automatically, whether to turn on an ambient light cancellation circuit, including:

if the intensity of the first ambient light signal is greater than a first preset threshold, turning on the ambient light cancellation circuit;

if the intensity of the first ambient light signal is lower than or equal to the first preset threshold, not turning on the ambient light cancellation circuit.

In an embodiment of the present disclosure, by means of comparing the intensity of the ambient light signal with a preset threshold, determination of whether to turn on the ambient light cancellation circuit is realized, which not only avoids a new interference caused by the ambient light cancellation circuit being turned on all the time, but may also save power.

In a possible implementation, the adjusting a cancellation signal intensity of the ambient light cancellation circuit automatically according to the intensity of the first ambient light signal to enable an intensity of the adjusted first ambient light signal to be within a preset range includes:

determining an electrical signal intensity of the first ambient light signal, where the electrical signal intensity of the first ambient light signal is an intensity after the first ambient light signal is converted into an electrical signal; and adjusting the cancellation signal intensity of the ambient light cancellation circuit dynamically to enable the intensity of the adjusted first ambient light signal to be lower than or equal to a second preset threshold, and obtaining a second ambient light signal, where the cancellation signal intensity is lower than or equal to the electrical signal intensity of the first ambient light signal.

In an embodiment of the present disclosure, by means of determining the electrical signal intensity of the first ambient light signal, and adjusting the cancellation signal intensity of the ambient light cancellation circuit dynamically, dynamic adjustment of the ambient light signal with different intensities is realized, thereby improving reliability of adjusting the ambient light signal acquired by the PPG sensor.

In a possible implementation, the ambient light signal adjustment method according to an embodiment of the present disclosure further includes:

receiving a mixed light signal acquired and output by the PPG sensor, where the mixed light signal comprises: a target light signal; and the first ambient light signal or the second ambient light signal; and where the target light signal is a light signal which is transmitted by a light transmitter and which, after passing through a human body, is received by a light receiver; and determining the target light signal through the mixed light signal and the first ambient light signal, or, determining the target light signal through the mixed light signal and the second ambient light signal.

In the solution, by means of determining the target light signal according to the mixed light signal and an adjusted ambient light signal, a physiological characteristic of a human body can be detected through the target light signal, thereby improving accuracy of detection.

In a possible implementation, the cancellation signal intensity is in direct proportion to the intensity of the first ambient light signal In a possible implementation, the ambient light cancellation circuit includes a successive approximation loop and a digitally controlled current source, and the successive approximation loop is connected to the digitally controlled current source.

The chip and the electronic equipment provided in embodiments of the present disclosure are introduced below. For contents and effects of the chip and the electronic equipment, reference may be made to the ambient light signal adjustment method provided in the first aspect or an optional implementation of the first aspect, and details are not repeated here.

In a second aspect, an embodiment of the present disclosure provides a chip, including:

a determining circuit and an ambient light cancellation circuit, where the determining circuit is connected to the ambient light cancellation circuit;

the determining circuit is configured to receive a first ambient light signal, where the first ambient light signal is an ambient light signal acquired and output by a photo plethysmor graph (PPG) sensor;

the determining circuit is further configured to determine, according to an intensity of the first ambient light signal automatically, whether to turn on the ambient light cancellation circuit;

the ambient light cancellation circuit is configured to adjust the first ambient light signal according to the intensity of the first ambient light signal;

the ambient light cancellation circuit is further configured to: if it is determined to turn on the ambient light cancellation circuit, adjust a cancellation signal intensity of the ambient light cancellation circuit automatically according to the intensity of the first ambient light signal to enable an intensity of the adjusted first ambient light signal to be within a preset range.

In a possible implementation, the determining circuit is specifically configured to:

if the intensity of the first ambient light signal is greater than a first preset threshold, turn on the ambient light cancellation circuit; or if the intensity of the first ambient light signal is lower than or equal to the first preset threshold, not turn on the ambient light cancellation circuit.

In a possible implementation, the ambient light cancellation circuit is specifically configured to:

determine an electrical signal intensity of the first ambient light signal, where the electrical signal intensity of the first ambient light signal is an intensity after the first ambient light signal is converted into an electrical signal; and adjust the cancellation signal intensity of the ambient light cancellation circuit dynamically to enable the intensity of the adjusted first ambient light signal to be lower than or equal to a second preset threshold, and obtain a second ambient light signal, where the cancellation signal intensity is lower than or equal to the electrical signal intensity of the first ambient light signal.

In a possible implementation, the chip according to an embodiment of the present disclosure further includes a processor, the processor is configured to:

receive a mixed light signal acquired and output by the PPG sensor, where the mixed light signal includes: a target light signal; and the first ambient light signal or the second ambient light signal; and where the target light signal is a light signal which is transmitted by a light transmitter and which, after passing through a human body, is received by a light receiver; and determine the target light signal through the mixed light signal and the first ambient light signal, or, determine the target light signal through the mixed light signal and the second ambient light signal.

In a possible implementation, the determining circuit includes a comparator.

In a possible implementation, the ambient light cancellation circuit includes a successive approximation loop and a digitally controlled current source, where a first terminal of the successive approximation loop is connected to the determining circuit, and a second terminal of the successive approximation loop is connected to the digitally controlled current source In a possible implementation, the chip according to an embodiment of the present disclosure further includes an amplifier and a driver, where a terminal of the amplifier is connected to a light receiver, and the driver is connected to a light transmitter;

the amplifier is configured to amplify a light signal received by the light receiver; and the driver is configured to drive the light transmitter to transmit a light signal.

In a possible implementation, the chip according to an embodiment of the present disclosure further includes an analog-to-digital converter and a digital-to-analog converter, where the analog-to-digital converter is configured to convert an analog signal output by the amplifier into a digital signal, or convert an analog signal output by the ambient light cancellation circuit into a digital signal;

the digital-to-analog converter is configured to convert a digital signal sent by a controller into an analog signal.

In a possible implementation, the photo plethysmor graph (PPG) sensor includes a light-emitting device and a photoelectric conversion device, and the chip further includes the photoelectric conversion device connected to the determining circuit.

In a possible implementation, the light-emitting device is integrated in the chip.

In a third aspect, an embodiment of the present disclosure provides electronic equipment, including: the chip provided in the second aspect and an optional implementation of the second aspect.

The present disclosure provides an ambient light signal adjustment method, a chip and electronic equipment, which allow for: receiving a first ambient light signal, where the first ambient light signal is an ambient light signal acquired and output by a photo plethysmor graph (PPG) sensor; then determining, according to an intensity of the first ambient light signal automatically, whether to turn on an ambient light cancellation circuit, where the ambient light cancellation circuit is configured to adjust the first ambient light signal according to the intensity of the first ambient light signal; and if it is determined to turn on the ambient light cancellation circuit, adjusting a cancellation signal intensity of the ambient light cancellation circuit automatically according to the intensity of the first ambient light signal to enable an intensity of the adjusted first ambient light signal to be within a preset range. In an embodiment of the present disclosure, by means of determining, according to the intensity of the ambient light signal, whether to turn on the ambient light cancellation circuit, and adjusting, after the ambient light cancellation circuit is turned on, the cancellation signal intensity of the ambient light cancellation circuit automatically to enable the intensity of the adjusted first ambient light signal to be within the preset range all the time, adjustment of the ambient light signal acquired by the PPG sensor is realized, thereby ensuring accuracy of a wearable device to detect a physiological characteristic of a user.

BRIEF DESCRIPTION OF DRAWINGS

To describe technical solutions in embodiments of the present disclosure or in the prior art more clearly, the following briefly introduces accompanying drawings needed for describing the embodiments or the prior art. Apparently, the accompanying drawings in the following description illustrate merely some embodiments of the present disclosure, and persons of ordinary skill in the art may still derive other drawings from these accompanying drawings without creative effort.

DETAILED DESCRIPTION OF EMBODIMENTS

To make objectives, technical solutions, and advantages of embodiments of the present disclosure clearer, the following clearly and comprehensively describes the technical solutions in embodiments of the present disclosure with reference to the accompanying drawings in embodiments of the present disclosure. Apparently, the described embodiments are merely a part rather than all embodiments of the present disclosure. All other embodiments obtained by persons of ordinary skill in the art based on embodiments of the present disclosure without creative effort shall fall into the protection scope of the present disclosure.

The terms "first", "second", "third", "fourth", etc. (if exists) in the specification, claims and the above accompanying drawings of the present disclosure are used to distinguish similar objects, but not intended to describe a specific order or sequence. It should be understood that data used in this way is interchangeable under appropriate circumstances, so that the embodiments of the present disclosure described herein can, for example, be implemented in a sequence other than those illustrated or described herein. In addition, the terms "including" and "having" and any variations of them are intended to cover non-exclusive inclusions. For example, processes, methods, systems, products or devices that include a series of steps or units are not necessarily limited to the clearly listed steps or units, but may include other steps or units that are not clearly listed or are inherent to these processes, methods, products, or devices.

With development of a smart device, the smart device also has more and more functions. In order to detect health status of a human body, a sensor (e.g., a sensor disposed in proximity to, above or close to an external body surface of the human body in other ways) in the smart device (e.g., a wearable device) can be used for detection. The wearable device is not only convenient to wear, but can also detect a variety of human health data at any time. At present, use of the wearable device to detect some health data of a wearer can be realized by photo detection. A signal light of certain wavelength is transmitted by a light transmitter in the wearable device to a wearer or an object to be detected, and the signal light is received by a light receiver, then the signal light received by the light receiver is analyzed to determine a characteristic of the wearer or the object to be detected. However, due to diversity of application environment, an intensity of the signal light received by the light receiver will be affected, resulting in an inaccurate detection result. In order to solve the above problems, the present disclosure proposes an ambient light signal adjustment method, a chip and electronic equipment.

Hereinafter, an exemplary application scenario of an embodiment of the present disclosure is introduced.

Figure 1:
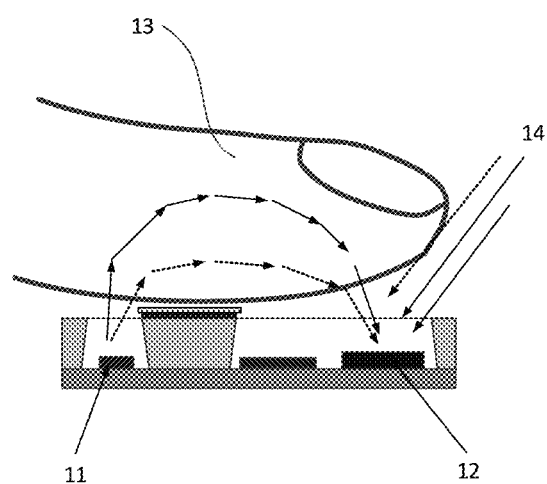
FIG. 1 is a diagram illustrating an exemplary application scenario according to a technical solution of the present disclosure.

In embodiments of the present disclosure, the application scenario of the embodiment of the present disclosure is not limited to heart rate detection. For example, it can also be used for a blood oxygen, an activity level, a blood pressure, a galvanic skin response, etc. The present disclosure only takes the heart rate detection as an example for introduction. An embodiment of the present disclosure can be applied to a heart rate detection chip. FIG. 1 is a diagram illustrating an exemplary application scenario according to a technical solution of the present disclosure. As shown in FIG. 1, light of a certain wavelength is transmitted by a light-emitting diode 11 and incident to a skin tissue 13, where, the light-emitting diode 11 can be one or more. Different light-emitting diodes 11 can be driven by one or more drivers in the heart rate detection chip, and the driver is connected to a dynamic control module in the heart rate detection chip. Different light-emitting diodes 11 can also emit light of different wavelengths, which is not limited in the embodiment of the present disclosure. After the light emitted by one or more light-emitting diodes 11 is reflected, scattered and absorbed by the skin tissue 13, part of the light can be emitted from the surface of the skin tissue 13 and received by a photodiode 12 of the heart rate detection chip. Through photoelectric conversion, the photodiode 12 can convert a received target light signal from a light signal into an electrical signal in terms of its form. As such, the photodiode 12 can be one or more, and different photodiodes 12 can perform amplification through one or more amplifiers, and a target light signal amplified by the amplifier can be converted from an analog signal to a digital signal through an analog-to-digital conversion. During this process, since a blood volume of the skin tissue 13 presents a pulsatile change responsive to a heart rhythm, an intensity of the target light signal received by the photodiode 12 also presents a pulsatile change accordingly. Upon analysis of the target light signal received by the photodiode 12, a heart rate value is calculated. However, while the photodiode 12 is receiving the light emitted by the light-emitting diode 11, it also receives an ambient light signal 14 from the environment. Due to changes in the environment, if an intensity of the ambient light signal 14 is too strong, the target signal light received by the photodiode 12 will be affected, resulting in an inaccurate heart rate detection result, so the intensity of the received ambient light signal needs to be adjusted. Based on this, the embodiments of the present disclosure provide an ambient light signal adjustment method, a chip and electronic equipment.

Based on the above application scenario, the technical solutions of the present disclosure will be described in detail below.

Figure 2:
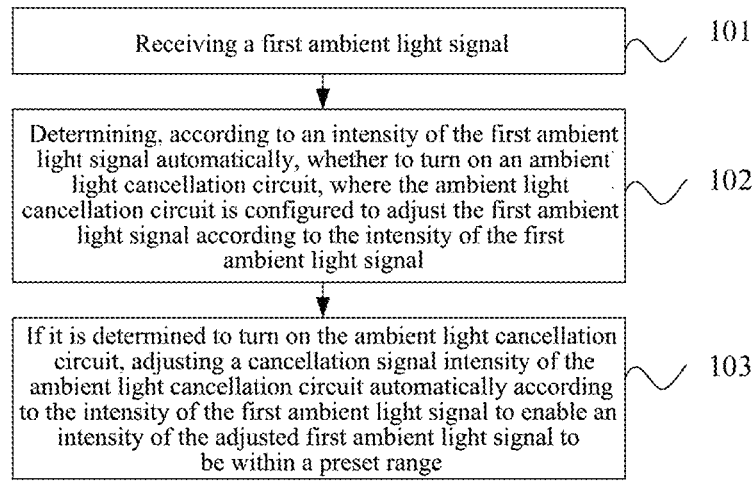
FIG. 2 is a flowchart of an ambient light signal adjustment method according to an embodiment of the present disclosure.

FIG. 2 is a flowchart of an ambient light signal adjustment method according to an embodiment of the present disclosure, where the method can be realized by means of software and/or hardware, for example: it may be part of a terminal device or the entire terminal device, the terminal device may be a wearable device, such as a heart rate bracelet, a heart rate headset, a health bracelet, a health watch, a blood oxygen bracelet, a blood oxygen watch and other optical wearable devices; or it may be a medical device, a fitness device, a chip in a terminal device, etc., the following describes the ambient light signal adjustment method with the terminal device as an executive body. As shown in FIG. 2, the ambient light signal adjustment method according to the present disclosure includes the following steps:

Step 101: Receiving a first ambient light signal.

The first ambient light signal is an ambient light signal acquired and output by a PPG sensor. During a photoelectric detection performed by the terminal device, since a light signal received by the terminal device may be affected by a change in an ambient light intensity, the first ambient light signal may be acquired before a light transmitter in the terminal device transmits a light signal. As such, the first ambient light signal may be an original ambient light signal that has not been adjusted by an amplifier, or it may be an ambient light signal adjusted by the amplifier, which is not limited in the embodiment of the present disclosure.

With regard to receiving the first ambient light signal, the first ambient light signal can be received by a light receiver in the terminal device, or the first ambient light signal transmitted by the PPG sensor may be received by a determining circuit, where the first ambient light signal transmitted by the PPG sensor is in an electrical signal form, and the embodiment of the present disclosure does not limit a specific way of receiving the first ambient light signal. The first ambient light signal can be represented by a light intensity signal, or the first ambient light signal can be converted into an electrical signal via a photoelectric conversion module, and an electrical signal can be used to represent the first ambient light signal. For example, a magnitude of current signal or a magnitude of voltage signal can be used to indicate an intensity of the first ambient light signal. As such, the greater the current signal of the first ambient light signal, the greater the intensity of the first ambient light signal, and the greater the impact on a subsequent detection result; the greater the voltage signal of the first ambient light signal, the greater the intensity of the first ambient light signal, and the greater the impact on a subsequent detection result. The embodiment of the present disclosure does not limit a representation form of the first ambient light signal.

Step 102: Determining, according to an intensity of the first ambient light signal automatically, whether to turn on an ambient light cancellation circuit, where the ambient light cancellation circuit is configured to adjust the first ambient light signal according to the intensity of the first ambient light signal.

The terminal device may be in different environments. For different environments, the first ambient light signal collected has different intensities. In a possible implementation, the intensity of the first ambient light signal is relatively small, which does not affect detection of a human physiological characteristic, so there is no need to process the ambient light signal. In another possible implementation, after the first ambient light signal is received, there may be a need to adjust the first ambient light signal. For example, when the ambient light is relatively intense, if the intensity of the first ambient light signal is too strong, it may exceed a tolerance range of a back-end circuit, or the intensity of the collected first ambient light signal is relatively strong, although it does not exceed a tolerance range of a back-end circuit, it may compress the amount of target light signals, resulting in a failure to accurately analyze a signal variation law of the target light signals, and then affecting detection results. In that way, the target light signal is a light signal which is transmitted by a light transmitter in the terminal device and which, after passing through a human body, is received by a light receiver.

In order to avoid the influence on the target light signal due to too strong intensity of the first ambient light signal, it can be determined, according to an intensity of the first ambient light signal, whether to turn on an ambient light cancellation circuit, where the ambient light cancellation circuit is configured to adjust the first ambient light signal according to the intensity of the first ambient light signal. The embodiment of the present disclosure does not limit a specific circuit structure of the ambient light cancellation circuit. In a possible implementation, the ambient light cancellation circuit may include a digitally controlled current source and a successive approximation loop to realize cancellation of the first ambient light signal. The embodiment of the present disclosure does not limit a specific implementation of determining, according to the intensity of the first ambient light signal, whether to turn on the ambient light cancellation circuit. In another possible implementation, it can be realized by setting a preset range, for example, when the intensity of the first ambient light signal is within a set OFF range, there is no need to turn on the ambient light cancellation circuit; if the intensity of the first ambient light signal is not within a set OFF range or is within a set ON range, the ambient light cancellation circuit needs to be turned on. In another possible implementation, the determining, according to the intensity of the first ambient light signal, whether to turn on the ambient light cancellation circuit includes:

if the intensity of the first ambient light signal is greater than a first preset threshold, turning on the ambient light cancellation circuit; if the intensity of the first ambient light signal is lower than or equal to the first preset threshold, not turning on the ambient light cancellation circuit.

With a way of setting a first preset threshold to determine whether to turn on the ambient light cancellation circuit, the implementation is simple, and by determining the intensity of the first ambient light signal, it is determined whether to turn on the ambient light cancellation circuit, avoiding introduction of new interference when the ambient light cancellation circuit is in an ON state all the time, thereby affecting a signal-to-noise ratio of the light signal, at the same time, avoiding impacts on a back-end circuit and a detection result due to a too strong intensity of the first ambient light signal when the ambient light canceling circuit is in an OFF state all the time or there is no ambient light canceling circuit.

As such, the embodiment of the present disclosure does not limit specific ranges and sizes of the set ON range, the set OFF range and the first preset threshold, provided that the intensity of the first ambient light signal can be used to determine whether there is a need to turn on the ambient light cancellation circuit so that detection accuracy can be improved. In a possible implementation, the first ambient light signal can be converted into an electrical signal in terms of form, and the intensity of the first ambient light signal can be indicated with a current of the electrical signal. At this time, the first preset threshold can take a maximum allowable current of the back-end circuit according to the embodiment of the present disclosure as a reference. For example, the first preset threshold can be 50% of the maximum allowable current, which is not limited in the embodiment of the present disclosure.

Step 103: If it is determined to turn on the ambient light cancellation circuit, adjusting a cancellation signal intensity of the ambient light cancellation circuit automatically according to the intensity of the first ambient light signal to enable an intensity of the adjusted first ambient light signal to be within a preset range.

If it is determined to turn on the ambient light cancellation circuit, the embodiment of the present disclosure does not limit a specific implementation of how to automatically adjust a cancellation signal intensity of the ambient light cancellation circuit according to the intensity of the first ambient light signal, provided that the intensity of the adjusted first ambient light signal can be kept within a preset range all the time. As such, the preset range can be realized by setting a preset maximum threshold and a preset minimum threshold. The embodiment of the present disclosure does not limit a specific range and implementation of the preset range, and setting can be made specifically according to user requirements.

In a possible implementation, the adjusting the cancellation signal intensity of the ambient light cancellation circuit automatically according to the intensity of the first ambient light signal to enable the intensity of the adjusted first ambient light signal to be within a preset range includes:

determining an electrical signal intensity of the first ambient light signal, where the electrical signal intensity of the first ambient light signal is an intensity after the first ambient light signal is converted into an electrical signal; and adjusting the cancellation signal intensity of the ambient light cancellation circuit dynamically to enable the intensity of the adjusted first ambient light signal to be lower than or equal to a second preset threshold, and obtaining a second ambient light signal, where the cancellation signal intensity is lower than or equal to the electrical signal intensity of the first ambient light signal.

Before the cancellation signal intensity of the ambient light cancellation circuit is adjusted, it is necessary to determine an electrical signal intensity of the first ambient light signal. The electrical signal intensity of the first ambient light signal is an intensity after the first ambient light signal is converted into an electrical signal. For example, the electrical signal of the first ambient light signal may be a current signal or a voltage signal, then the electrical signal intensity of the first ambient light signal is a magnitude of current or a magnitude of voltage. The embodiment of the present disclosure does not limit a type of the electrical signal of the first ambient light signal. For different environments, weather and other factors, the electrical signal intensity of the first ambient light signal acquired before each sampling may also be different. Through the electrical signal intensity of the first ambient light signal, the cancellation signal intensity of the ambient light cancellation circuit can be dynamically adjusted, and the cancellation signal intensity is lower than or equal to the electrical signal intensity of the first ambient light signal, for example, the intensity of the cancellation signal is positively correlated with the intensity of the electrical signal of the first ambient light signal. For example, the intensity of the cancellation signal is positively correlated with the intensity of the electrical signal of the first ambient light signal, such that the electrical signal intensity of the adjusted first ambient light signal is lower than or equal to the second preset threshold, or an electrical signal intensity of an adjusted second ambient light signal is within the preset range. The embodiment of the present disclosure does not limit this. In the embodiment of the present disclosure, the cancellation signal intensity of the ambient light cancellation circuit is dynamically adjusted through the electrical signal intensity of the first ambient light signal, thereby realizing dynamic adjustment for ambient light signals of different intensities, and improving reliability of ambient light signal adjustment.

As such, the embodiment of the present disclosure does not limit a value of the second preset threshold, provided that detection accuracy can be improved by adjusting the intensity of the first ambient light signal. In a possible implementation, the electrical signal intensity of the first ambient light signal is indicated with a current. At this time, the second preset threshold can take a maximum allowable current of the back-end circuit according to the embodiment of the present disclosure as a reference. For example, the second preset threshold can be 10% of the maximum allowable current, which is not limited in the embodiment of the present disclosure.

In the embodiment of the present disclosure, by means of determining, according to the intensity of the ambient light signal, whether to turn on the ambient light cancellation circuit, and adjusting, after the ambient light cancellation circuit is turned on, the cancellation signal intensity of the ambient light cancellation circuit automatically to enable the intensity of the adjusted first ambient light signal to be within the preset range all the time, adjustment of the ambient light signal acquired by the PPG sensor is realized, thereby ensuring accuracy of a wearable device to detect a physiological characteristic of a user.

Figure 3:
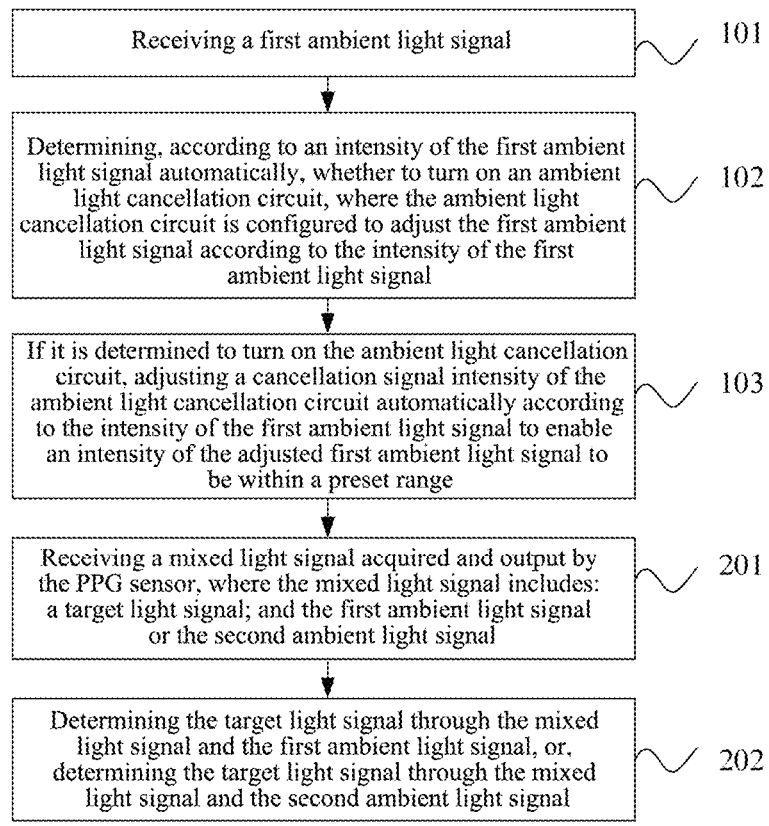
FIG. 3 is a flowchart of an ambient light signal adjustment method according to another embodiment of the present disclosure.

In a possible implementation, FIG. 3 is a flowchart of an ambient light signal adjustment method according to another embodiment of the present disclosure, where the method can be realized by means of software and/or hardware, for example: it may be part of a terminal device or the entire terminal device, the terminal device may be a wearable device, such as a heart rate bracelet, a heart rate headset, a health bracelet, a health watch, a blood oxygen bracelet, a blood oxygen watch and other optical wearable devices; or it may also be a medical device, a fitness device, a chip in a terminal device, etc., the following describes the ambient light signal adjustment method with the terminal device as an executive body. As shown in FIG. 3, the ambient light signal adjustment method according to the present disclosure may further include the following steps.

Step 201: Receiving a mixed light signal acquired and output by the PPG sensor, where the mixed light signal includes: a target light signal; and the first ambient light signal or the second ambient light signal.

The mixed light signal can be a mixed light signal received by a light receiver in the terminal device, or the mixed light signal acquired and output by the PPG sensor through a transmission interface of a processor, where the mixed light signal output by the PPG sensor is an electrical signal in terms of form. After determining, according to the first ambient light signal, whether to turn on the ambient light cancellation circuit, if it is determined to turn on the ambient light cancellation circuit, the first ambient light signal is adjusted by the ambient light cancellation circuit to obtain a second ambient light signal. At this time, the mixed light signal includes a target light signal and the second ambient light signal. If it is determined to turn off the ambient light cancellation circuit, the first ambient light signal remains unchanged. At this time, the mixed light signal includes a target light signal and the first ambient light signal. In that way, the target light signal is a light signal which is transmitted by a light transmitter and which, after passing through a human body, is received by a light receiver, and the terminal device detects a physiological characteristic of a user by processing the target light signal.

Step 202: Determining the target light signal through the mixed light signal and the first ambient light signal, or, determining the target light signal through the mixed light signal and the second ambient light signal.

After the mixed light signal is received, if the mixed light signal includes a target light signal and the second ambient light signal, then the target light signal can be obtained by subtracting the second ambient light signal from the mixed light signal. If the mixed light signal includes a target light signal and the first ambient light signal, then the target light signal can be obtained by subtracting the first ambient light signal from the mixed light signal.

In the solution, by means of determining the target light signal according to the mixed light signal and an adjusted ambient light signal, a physiological characteristic of a human body can be detected through the target light signal, which improves accuracy of detection.

Figure 4:
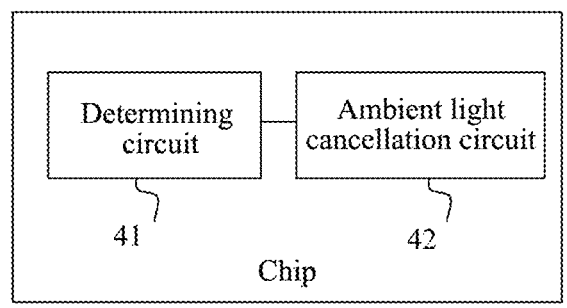
FIG. 4 is a schematic structural diagram of a chip according to an embodiment of the present disclosure.

An embodiment of the present disclosure provides a chip, FIG. 4 is a schematic structural diagram of a chip according to an embodiment of the present disclosure. As shown in FIG. 4, the chip according to the embodiment of the present disclosure can include:

a determining circuit 41 and an ambient light cancellation circuit 42, where the determining circuit 41 is connected to the ambient light cancellation circuit 42;

the determining circuit 41 is configured to receive a first ambient light signal, where the first ambient light signal is an ambient light signal acquired and output by a photo plethysmor graph (PPG) sensor;

the determining circuit 41 is further configured to determine, according to an intensity of the first ambient light signal automatically, whether to turn on the ambient light cancellation circuit;

the ambient light cancellation circuit 42 is configured to adjust the first ambient light signal according to the intensity of the first ambient light signal;

the ambient light cancellation circuit 42 is further configured to: if it is determined to turn on the ambient light cancellation circuit, adjust a cancellation signal intensity of the ambient light cancellation circuit automatically according to the intensity of the first ambient light signal to enable an intensity of the adjusted first ambient light signal to be within a preset range.

In a possible implementation, the determining circuit 41 is specifically configured to:

if the intensity of the first ambient light signal is greater than a first preset threshold, turn on the ambient light cancellation circuit; if the intensity of the first ambient light signal is lower than or equal to the first preset threshold, not turn on the ambient light cancellation circuit.

In a possible implementation, the ambient light cancellation circuit 42 is specifically configured to:

determine an electrical signal intensity of the first ambient light signal, where the electrical signal intensity of the first ambient light signal is an intensity after the first ambient light signal is converted into an electrical signal; and adjust the cancellation signal intensity of the ambient light cancellation circuit dynamically to enable the intensity of the adjusted first ambient light signal to be lower than or equal to a second preset threshold, and obtain a second ambient light signal, where the cancellation signal intensity is lower than or equal to the electrical signal intensity of the first ambient light signal.

Figure 5:
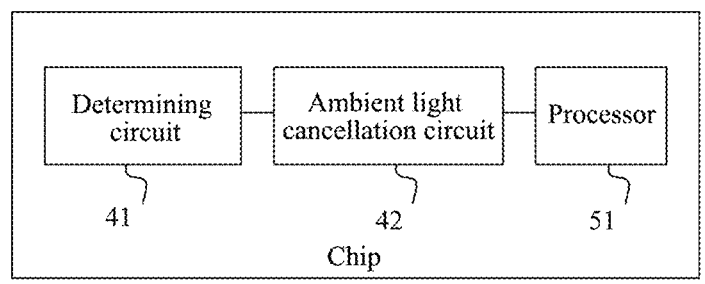
FIG. 5 is a schematic structural diagram of a chip according to a further embodiment of the present disclosure.

In a possible implementation, FIG. 5 is a schematic structural diagram of a chip according to a further embodiment of the present disclosure. As shown in FIG. 5, the chip according to the embodiment of the present disclosure can further include: a processor 51, the processor 51 is configured to: receive a mixed light signal acquired and output by the PPG sensor, where the mixed light signal includes: a target light signal; and the first ambient light signal or the second ambient light signal; and where the target light signal is a light signal which is transmitted by a light transmitter and which, after passing through a human body, is received by a light receiver.

Figure 6A:
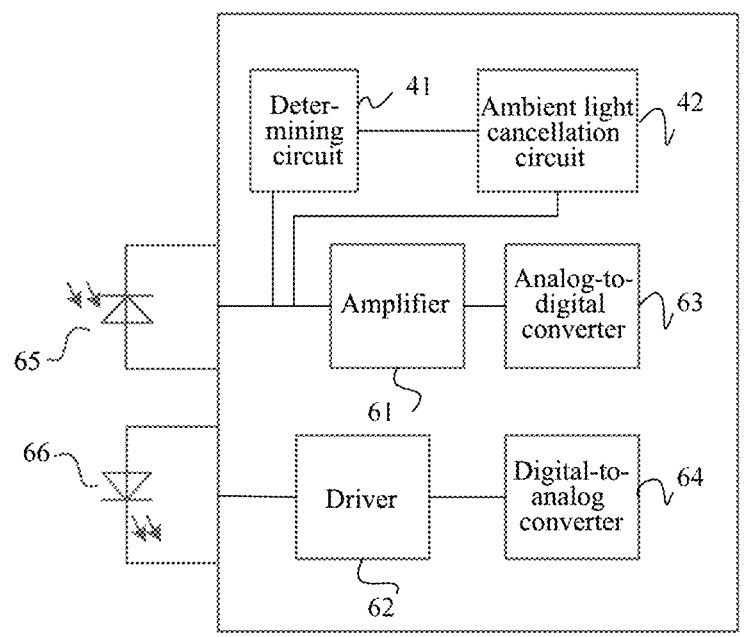
FIG. 6A is a schematic structural diagram of a chip according to another embodiment of the present disclosure.
Figure 6B:
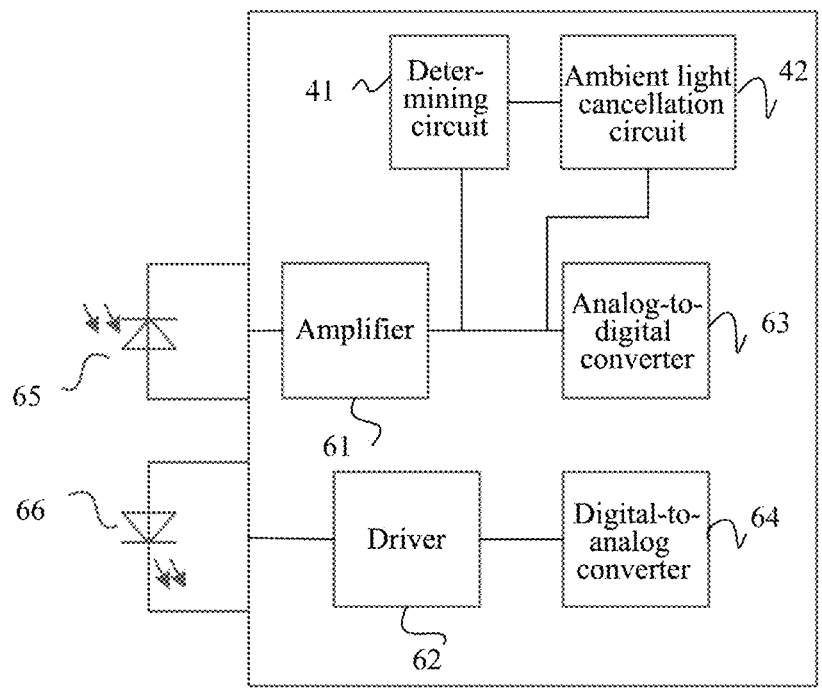
FIG. 6B is a schematic structural diagram of a chip according to another embodiment of the present disclosure.

Determine the target light signal through the mixed light signal and the first ambient light signal, or, determine the target light signal through the mixed light signal and the second ambient light signal. In a possible implementation, FIG. 6A-FIG. 6B are schematic structural diagrams of a chip according to another embodiment of the present disclosure. As shown in FIG. 6A or FIG. 6B, the chip according to the embodiment of the present disclosure can further include: an amplifier 61 and a driver 62. As shown in FIG. 6A, the determining circuit 41 and the ambient light cancellation circuit 42 can be disposed between the amplifier 61 and a light receiver 65; as shown in FIG. 6B, the determining circuit 41 and the ambient light cancellation circuit 42 can also be disposed between the amplifier 61 and an analog-to-digital converter 63, the embodiment of the present disclosure does not limit this.

A terminal of the amplifier 61 is connected to the light receiver 65, and the driver 62 is connected to a light transmitter 66.

The amplifier 61 is configured to amplify a light signal received by the light receiver 65; and the driver 62 is configured to drive the light transmitter 66 to transmit a light signal.

In a possible implementation, as shown in FIG. 6A or FIG. 6B, the chip according to the embodiment of the present disclosure further includes the analog-to-digital converter 63 and a digital-to-analog converter 64.

As shown in FIG. 6A, the analog-to-digital converter 63 is configured to convert an analog signal output by the amplifier into a digital signal. As shown in FIG. 6B, the analog-to-digital converter 63 is configured to convert an analog signal output by the ambient light cancellation circuit into a digital signal. The digital-to-analog converter 64 is configured to convert a digital signal sent by a controller into an analog signal.

Figure 7:
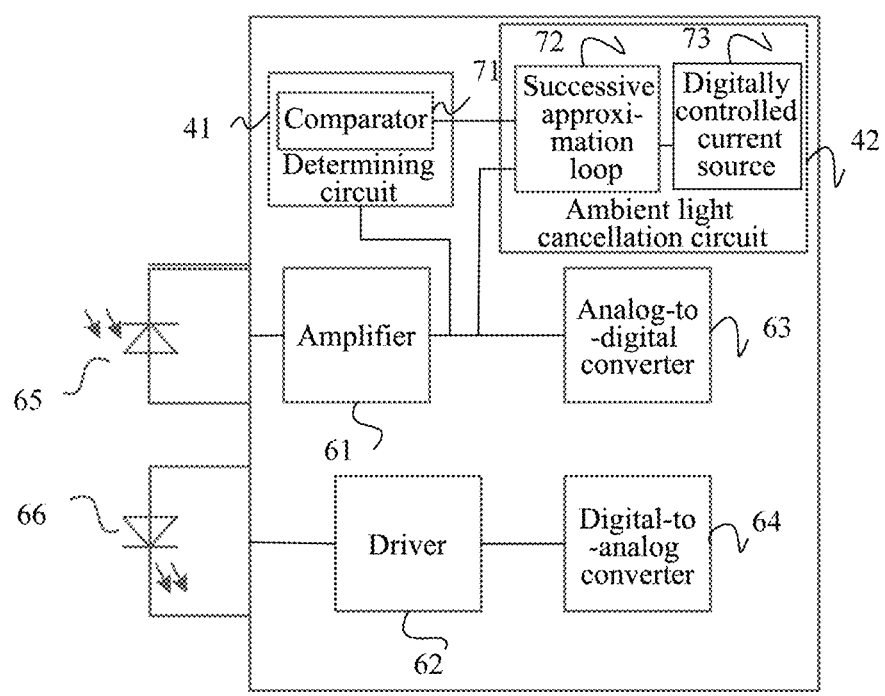
FIG. 7 is a schematic structural diagram of a chip according to still another embodiment of the present disclosure.

The embodiment of the present disclosure does not limit a specific circuit structure of the determining circuit. In a possible implementation, based on the above FIG. 6B, FIG. 7 is a schematic structural diagram of a chip according to still another embodiment of the present disclosure. As shown in FIG. 7, the determining circuit 41 includes a comparator 71.

Figure 8:
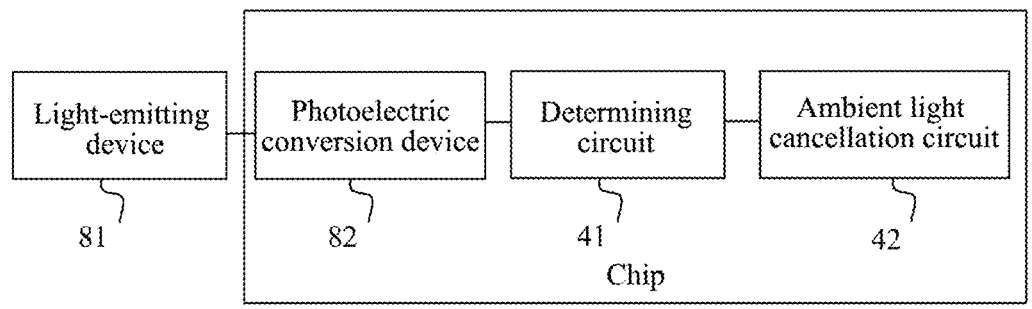
FIG. 8 is a schematic structural diagram of a chip according to yet still further embodiment of the present disclosure.

The embodiment of the present disclosure does not limit a specific circuit structure of the ambient light cancellation circuit. In a possible implementation, as shown in FIG. 7, the ambient light cancellation circuit 42 includes a successive approximation loop 72 and a digitally controlled current source 73, where a first terminal of the successive approximation loop 72 is connected to the determining circuit 41, and a second terminal of the successive approximation loop 72 is connected to the digitally controlled current source 73. In a possible implementation, on the basis of the above embodiment, an example is taken based on FIG. 4, FIG. 8 is a schematic structural diagram of a chip according to yet still further embodiment of the present disclosure. As shown in FIG. 8, the photo plethysmor graph (PPG) sensor includes a light-emitting device 81 and a photoelectric conversion device 82, and the chip also includes a photoelectric conversion device 82 connected to the determining circuit 41.

Figure 9:
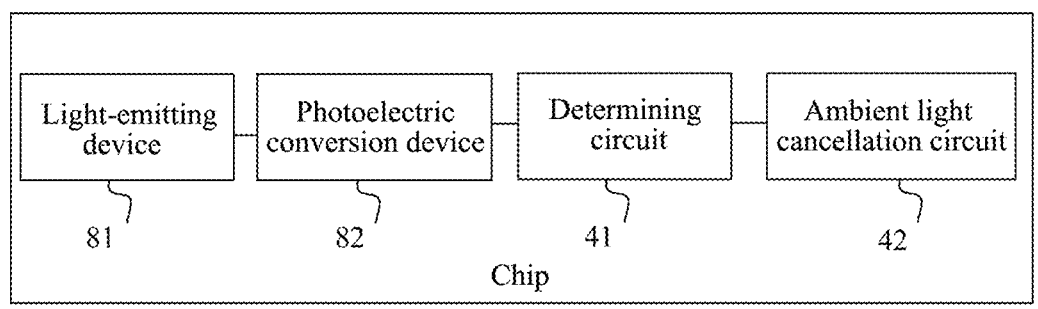
FIG. 9 is a schematic structural diagram of a chip according to yet a further embodiment of the present disclosure.

In a possible implementation, on the basis of the above embodiment, an example is taken based on FIG. 4, FIG. 9 is a schematic structural diagram of a chip according to yet a further embodiment of the present disclosure. As shown in FIG. 9, the light-emitting device 81 of the photo plethysmor graph (PPG) sensor is integrated in the chip.

Figure 10:
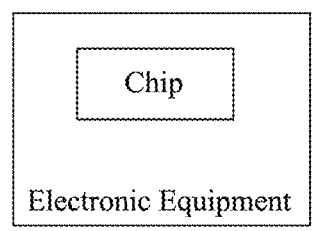
FIG. 10 is a schematic structural diagram of electronic equipment according to an embodiment of the present disclosure.

An embodiment of the present disclosure provides electronic equipment. FIG. 10 is a schematic structural diagram of the electronic equipment according to an embodiment of the present disclosure. As shown in FIG. 10, the electronic equipment according to the embodiment of the present disclosure includes the chip according to the above embodiments.

Finally, it should be noted that the foregoing embodiments are merely intended for describing the technical solutions of the present disclosure other than limiting the present disclosure. Although the present disclosure has been described in detail with reference to the foregoing embodiments, persons of ordinary skill in the art should understand that they may still make modifications to the technical solutions described in the foregoing embodiments or make equivalent substitutions to some or all technical features thereof, however, these modifications or substitutions do not make essence of a corresponding technical solution depart from the scope of the technical solutions in the embodiments of the present disclosure.

What is claimed is:

1. An ambient light signal adjustment method, comprising:
   receiving a first ambient light signal, wherein the first ambient light signal is an ambient light signal acquired and output by a photo plethysmor graph (PPG) sensor;
   determining, according to an intensity of the first ambient light signal automatically, whether to turn on an ambient light cancellation circuit, wherein the ambient light cancellation circuit is configured to adjust the first ambient light signal according to the intensity of the first ambient light signal; and
   if it is determined to turn on the ambient light cancellation circuit, adjusting a cancellation signal intensity of the ambient light cancellation circuit automatically according to the intensity of the first ambient light signal to enable an intensity of the adjusted first ambient light signal to be within a preset range.

2. The ambient light signal adjustment method according to claim 1, wherein the determining, according to an intensity of the first ambient light signal automatically, of whether to turn on an ambient light cancellation circuit comprises:
   if the intensity of the first ambient light signal is greater than a first preset threshold, turning on the ambient light cancellation circuit.

3. The ambient light signal adjustment method according to claim 1, wherein the determining, according to an intensity of the first ambient light signal, of whether to turn on an ambient light cancellation circuit comprises:
   if the intensity of the first ambient light signal is lower than or equal to the first preset threshold, not turning on the ambient light cancellation circuit.

4. The ambient light signal adjustment method according to claim 2, wherein the adjusting a cancellation signal intensity of the ambient light cancellation circuit automatically according to the intensity of the first ambient light signal to enable an intensity of the adjusted first ambient light signal to be within a preset range comprises:
   determining an electrical signal intensity of the first ambient light signal, wherein the electrical signal intensity of the first ambient light signal is an intensity after the first ambient light signal is converted into an electrical signal; and
   adjusting the cancellation signal intensity of the ambient light cancellation circuit dynamically to enable the intensity of the adjusted first ambient light signal to be lower than or equal to a second preset threshold, and obtaining a second ambient light signal, wherein the cancellation signal intensity is lower than or equal to the electrical signal intensity of the first ambient light signal.

5. The ambient light signal adjustment method according to claim 4, further comprising:
   receiving a mixed light signal acquired and output by the PPG sensor, wherein the mixed light signal comprises: a target light signal; and the first ambient light signal or the second ambient light signal; and wherein the target light signal is a light signal which is transmitted by a light transmitter and which, after passing through a human body, is received by a light receiver; and
   determining the target light signal through the mixed light signal and the first ambient light signal, or, determining the target light signal through the mixed light signal and the second ambient light signal.

6. The ambient light signal adjustment method according to claim 1, wherein the cancellation signal intensity is in direct proportion to the intensity of the first ambient light signal.

7. The ambient light signal adjustment method according to claim 1, wherein the ambient light cancellation circuit comprises a successive approximation loop and a digitally controlled current source, and the successive approximation loop is connected to the digitally controlled current source.

8. A chip, comprising: a determining circuit and an ambient light cancellation circuit, wherein the determining circuit is connected to the ambient light cancellation circuit;
the determining circuit is configured to receive a first ambient light signal, wherein the first ambient light signal is an ambient light signal acquired and output by a photo plethysmor graph (PPG) sensor;
the determining circuit is further configured to determine, according to an intensity of the first ambient light signal automatically, whether to turn on the ambient light cancellation circuit;
the ambient light cancellation circuit is configured to adjust the first ambient light signal according to the intensity of the first ambient light signal;
the ambient light cancellation circuit is further configured to: if it is determined to turn on the ambient light cancellation circuit, adjust a cancellation signal intensity of the ambient light cancellation circuit automatically according to the intensity of the first ambient light signal to enable an intensity of the adjusted first ambient light signal to be within a preset range.

9. The chip according to claim 8, wherein the determining circuit is configured to:
if the intensity of the first ambient light signal is greater than a first preset threshold, turn on the ambient light cancellation circuit.

10. The chip according to claim 8, wherein the determining circuit is configured to:
if the intensity of the first ambient light signal is lower than or equal to the first preset threshold, not turn on the ambient light cancellation circuit.

11. The chip according to claim 9, wherein the ambient light cancellation circuit is configured to:
determine an electrical signal intensity of the first ambient light signal, wherein the electrical signal intensity of the first ambient light signal is an intensity after the first ambient light signal is converted into an electrical signal; and
adjust the cancellation signal intensity of the ambient light cancellation circuit dynamically to enable the intensity of the adjusted first ambient light signal to be lower than or equal to a second preset threshold, and obtain a second ambient light signal, wherein the cancellation signal intensity is lower than or equal to the electrical signal intensity of the first ambient light signal.

12. The chip according to claim 11, further comprising: a processor,
the processor is configured to receive a mixed light signal acquired and output by the PPG sensor, wherein the mixed light signal comprises: a target light signal; and the first ambient light signal or the second ambient light signal; and wherein the target light signal is a light signal which is transmitted by a light transmitter and which, after passing through a human body, is received by a light receiver; and
determine the target light signal through the mixed light signal and the first ambient light signal.

13. The chip according to claim 11, further comprising: a processor,
the processor is configured to receive a mixed light signal acquired and output by the PPG sensor, wherein the mixed light signal comprises: a target light signal; and the first ambient light signal or the second ambient light signal; and wherein the target light signal is a light signal which is transmitted by a light transmitter and which, after passing through a human body, is received by a light receiver; and
determine the target light signal through the mixed light signal and the second ambient light signal.

14. The chip according to claim 8, wherein the determining circuit comprises a comparator.

15. The chip according to claim 14, wherein the ambient light cancellation circuit comprises a successive approximation loop and a digitally controlled current source, and
a first terminal of the successive approximation loop is connected to the determining circuit, and a second terminal of the successive approximation loop is connected to the digitally controlled current source.

16. The chip according to claim 15, further comprising: an amplifier and a driver,
wherein a terminal of the amplifier is connected to a light receiver, and the driver is connected to a light transmitter; and
the amplifier is configured to amplify a light signal received by the light receiver; and the driver is configured to drive the light transmitter to transmit a light signal.

17. The chip according to claim 16, further comprising an analog-to-digital converter and a digital-to-analog converter,
wherein the analog-to-digital converter is configured to convert an analog signal output by the amplifier into a digital signal, or convert an analog signal output by the ambient light cancellation circuit into a digital signal; and
the digital-to-analog converter is configured to convert a digital signal sent by a controller into an analog signal.

18. The chip according to claim 8, wherein the photo plethysmor graph (PPG) sensor comprises a light-emitting device and a photoelectric conversion device, and the chip further comprises the photoelectric conversion device connected to the determining circuit.

19. The chip according to claim 18, wherein the light-emitting device is integrated in the chip.

20. Electronic equipment, comprising: the chip according to claim 8.

* * * * *